United States Patent [19]  [11] 3,959,317
Thiem et al.  [45] May 25, 1976

[54] PROCESS FOR THE PREPARATION OF 1-NITROANTHRAQUINONE

[75] Inventors: Karl-Werner Thiem, Cologne; Wolfgang Auge, Odenthal-Hahnenberg; Rütger Neeff, Leverkusen, all of Germany

[73] Assignee: Bayer Aktiengesellschaft, Leverkusen, Germany

[22] Filed: July 9, 1975

[21] Appl. No.: 594,254

Related U.S. Application Data

[63] Continuation-in-part of Ser. No. 432,452, Jan. 11, 1974, abandoned.

[30] Foreign Application Priority Data

Jan. 13, 1973 Germany............................ 2301735

[52] U.S. Cl. ............................................... 260/369
[51] Int. Cl.$^2$.................. C07C 79/10; C07C 79/36; C09B 1/00
[58] Field of Search ..................................... 260/369

[56] References Cited

UNITED STATES PATENTS

| | | | |
|---|---|---|---|
| 3,766,222 | 10/1973 | Hartwig et al. | 260/369 |
| 3,798,243 | 3/1974 | Toth | 260/369 |
| 3,836,601 | 9/1974 | Frey et al. | 260/369 |

*Primary Examiner*—Paul F. Shaver
*Attorney, Agent, or Firm*—Plumley & Tyner

[57] ABSTRACT

Process for the preparation of 1-nitroanthraquinone by nitration of anthraquinone in the presence of highly concentrated nitric acid, characterised in that nitration is carried out at temperatures of 20° to 80°C, the reaction is terminated by lowering the nitric acid molar fraction in the reaction mixture to ≤ 0.85 by distilling off concentrated nitric acid and 1-nitroanthraquinone is precipitated by subsequently adjusting the nitric acid molar fraction to ≤ 0.7 to 0.4 and is separated off in a manner which is in itself known.

5 Claims, No Drawings

PROCESS FOR THE PREPARATION OF 1-NITROANTHRAQUINONE

This application is a continuation-in-part of U.S. Ser. No. 432,452, filed Jan, 11, 1974, now abandoned.

It is generally known to carry out the nitration of anthraquinone in highly concentrated nitric acid and to stop the reaction by introducing the reaction mixture into a large amount of water or ice.

German Offenlegungsschrift (German Published Specification) 2,162,538 describes an improved process for the preparation of 1-nitroanthraquinone, in which anthraquinone is nitrated in the presence of at least 20 mol of nitric acid ($\geq 90\%$) at temperatures between $-40°$ and $+35°C$. This literature reference discloses that the most favourable conditions when using 98% strength nitric acid are if the molar ratio is approx. 40:1 relative to anthraquinone and the temperatures are from $-5°$ to $+15°C$. In the case of this procedure, the reaction, which takes 3 to 25 minutes, occurs so rapidly that it is necessary to stop it by adding ice and thereby to adjust the acid concentration to 60–85% strength in order as far as possible to prevent the formation of further undesired by-products.

German Offenlegungsschrift (German Published Specification) No. 2,220,377, which describes a further improved process for the nitration of anthraquinone in excess nitric acid, teaches that regulating the reaction speed by adding water is very disadvantageously associated with the formation of large amounts of diluten nitric acid which can only be brought back to a higher concentration with great expenditure of energy, time and apparatus. Hence, dilute nitric acid is used instead of water for stopping the reaction. However, this process still has considerable disadvantages since considerable volumes of dilute nitric acid are additionally introduced into the reaction mixture and the rectification cycle for the recovery of both highly concentrated nitric acid and dilute nitric acid is severely strained because of the very high total volumes. This is because, in order to stop the reaction, so much dilute nitric acid has to be added that the reaction volume is at least doubled, resulting in considerable expenditure on apparatus and energy.

It has now been found, surprisingly, that 1-nitroanthraquinone can be prepared and purified very successfully even without producing large amounts of dilute nitric acid if anthraquinone is nitrated in the presence of highly concentrated nitric acid, especially in $\geq 90\%$ strength nitric acid, and the reaction is stopped by lowering the molar fraction of nitric acid by distilling off nitric acid. In the text which follows, molar fraction is always to be understood as the fraction of nitric acid in the particular total mixture, according to the following equation:

$$\gamma HNO_3 = n_{HNO_3}/(n_{HNO_3} + n_N + n_{H_2O})$$

$n$ = number of mols
$N$ = nitroanthraquinones + anthraquinone.

The process according to the invention is characterised in that anthraquinone is nitrated in the presence of highly concentrated nitric acid (especially in $>90\%$ strength nitric acid) in the temperature range of $+20°$ to $+80°C$ and the reaction is stopped by adjusting the molar fraction of nitric acid to a value of $\leq 0.85$, by distilling off concentrated nitric acid, and that subsequently the molar fraction of nitric acid is adjusted to a value of about 0.7 to about 0.4, for example again by distilling off nitric acid and/or dilution with water and/or with dilute nitric acid, and the 1-nitroanthraquinone which has precipitated is separated from the by-products which largely remain in the filtrate and is thus purified. The by-products can be precipitated from the filtrate by lowering the molar fraction of nitric acid to $\leq 0.4$.

It is well-known that the nitration of anthraquinone can take place successfully at almost any molar ratio of nitric acid to anthraquinone, provided that nitric acid is employed in excess. For example molar ratios of nitric acid to anthraquinone up to 40:1 or higher can be employed. Molar ratios of nitric acid to anthraquinone of less than 20:1, especially 6:1 to 15:1 are preferred, but molar ratios of greater than 20:1, for example in the range of 20:1 to 80:1 are suitable and operable as well with the only disadvantage being that larger volumes of nitric acid are to be handled. The present invention relates to a method for terminating the nitration reaction of anthraquinone to 1-nitroanthraquinone and recovering 1-nitroanthraquinone in a high yield and a high purity.

Distilling off concentrated nitric acid according to the present invention for stopping the nitration reaction and precipitating 1-nitroanthraquinone can take place at normal or reduced pressure, for example at a pressure in the range of from 150 to 760 mm Hg, especially in the range of from 200 to 500 mm Hg. The optimum values of the molar fraction for stopping the nitration reaction and the optimum values of the molar fraction for precipitating 1-nitroanthraquinone depend on the temperature. For obtaining optimum results at higher or lower temperatures, correspondingly lower or higher molar fractions are to be selected within the given ranges. It is further advantageous to cool the reaction mixture for precipitating 1-nitroanthraquinone, for example to temperatures below 15°C, especially below 0°C.

The following possible combinations exist, according to the process of the invention, for stopping the reaction and for the subsequent purification operation:

The reaction is stopped by distilling off nitric acid. The molar fraction required for the precipitation of 1-nitroanthraquinone can be obtained by adding water and/or dilute nitric acid and/or by distilling off nitric acid.

If distilling off nitric acid results in a molar ratio of the nitration products and unreacted anthraquinone to nitric acid of $\leq 12:1$ or if the nitration is carried out at these molar ratios, the 1-nitroanthraquinone precipitated at temperatures of $\leq 15°C$ can be separated from the by-products present in the filtrate. These by-products can be precipitated almost completely from the filtrate if a molar ratio of $\leq 0.4$ is selected, for example by dilution with water or by partially or completely distilling off the nitric acid. This mixture of the by-products which has been precipitated and separated off in the usual manner contains almost the entire 2-nitroanthraquinone. The latter can be isolated in a relatively pure form if the precipitation described above is carried out fractionally. For example, the nitric acid freed from the organic product can be re-concentrated and then recycled to the process, or be recycled to the process as a diluent.

The nitration can be carried out according to the process of the invention in customary reactors, such as a flow tube, kettle cascade or kettle, in continuous or discontinuous operation. In order to achieve as high a yield of 1-nitroanthraquinone as possible in continuous operation, pronounced plug flow or Reynolds numbers >2,300 should be achieved in the case of the flow tube whilst an ideal dwell time spectrum should be achieved in the case of the cascade or kettle. The process according to the invention can, for example, be carried out in the form of the following procedure:

The nitration is stopped by feeding the entire reaction mixture to an evaporator, for example a contact thin layer evaporator, distilling off — preferably rapidly — the requisite portion of nitric acid and either cooling the mixture present in the sump to temperatures ≤ 15° in a crystallisation apparatus or, after prior addition of water or dilute nitric acid, precipitating the 1-nitroanthraquinone and separating it off in a separation apparatus. The distillate is converted into a high strength nitric acid and a low strength nitric acid, using a column. By-products dissolved in the filtrate can be precipitated therefrom either by dilution with water or by distilling off the nitric acid. The nitric acid freed of organic products can be recycled to the process, for example after re-concentration, or for use as a diluent.

The advantages of the process according to the invention are that the reaction is stopped merely by relatively slight changes of conditions (molar fraction), and that subsequently satisfactory purification of 1-nitroanthraquinone is achieved. In particular, the advantages are that the reaction is stopped merely by distilling off nitric acid as a result, the volumes of nitric acid to be handled can be kept relatively small. The same is true of the subsequent purification operation.

In the examples which follow, molar ratio always means that of nitric acid/anthraquinone. Unless otherwise stated, the product is isolated at room temperature. The yield is always relative to anthraquinone employed. The degrees quoted are °C.

EXAMPLE 1

208 g of anthraquinone are stirred with 1,210 g of 99% strength nitric acid (molar ratio of nitric acid/anthraquinone = 19:1) for 26 minutes at 25°, resulting in a molar fraction of 0.87. To terminate the reaction, 566 g of 99% strength nitric acid are distilled off rapidly so that subsequently the molar fraction in the sump is 0.79. On adding 112 g of water, the temperature of the sump rises and on slow cooling the desired product separates out. (Molar fraction $\gamma HNO_3 = 0.52$). After centrifuging off at room temperature, rinsing with 75% strength nitric acid, washing until neutral and drying, 204 g of 89.4% strength 1-nitroanthraquinone are obtained (72% of theory).

EXAMPLE 2

If 208 g of anthraquinone are stirred in 764 g of nitric acid (99% strength) (molar ratio 12:1) for 18 minutes at 45°, 191 g of nitric acid (99% strength) are distilled off rapidly to stop the reaction (molar fraction in the sump 0.78) and subsequently 1,550 g of 68% strength nitric acid are added (molar fraction 0.45), the desired product precipitates in a readily filtrable form on slow cooling. After working up as described in Example 1, 200 g of 91% strength 1-nitroanthraquinone are obtained (72% of theory).

EXAMPLE 3

A mixture of 208 g of anthraquinone and 573 g of 99% strength nitric acid (molar ratio 9:1) is stirred for 45 minutes at 60°. After distilling off 127 g of nitric acid (99% strength) the sump (molar fraction 0.73) is slowly cooled to −5°. The product which has precipitated is centrifuged off at this temperature, washed with 68% strength nitric acid and freed from adhering nitric acid in vacuo. Yield: 205 g of an 84% strength 1-nitroanthraquinone (68% of theory).

EXAMPLE 4

1.16 kg per hour of anthraquinone are nitrated with 12.94 kg per hour of 95% strength nitric acid (molar ratio 35:1) in a flow tube reactor at 45°C with a dwell time of 15 minutes. 9.14 kg per hour of 99% strength nitric acid are distilled off to stop the reaction (molar fraction 0.60). After addition of 4.41 kg per hour of 70% strength nitric acid to the sump product of the destillation (molar fraction 0.47) 1.10 kg per hour of 1-nitroanthraquinone are obtained by filtration (yield 70.2% of theory, purity 90%).

EXAMPLE 5

208 g anthraquinone are nitrated with 5.6 kg of 90% strength nitric acid (molar ratio 80:1) at 65°C during 2.5 hours. Thereafter 3.46 kg of 98% strength nitric acid are distilled off (molar fraction 0.45). After cooling to room temperature 1-nitroanthraquinone separates. After filtration, washing with 67.5% strength nitric acid and drying 200.2 g 1-nitroanthraquinone are obtained (yield 72% of theory, purity 91%).

EXAMPLE 6

208 g anthraquinone are nitrated with 2.32 kg of 95% strength nitric acid (molar ratio 35:1) at 25°C during 1.5 hours. The reaction is stopped by distilling off 1.74 kg of 94% strength nitric acid (molar fraction 0.73). 1-nitroanthraquinone is obtained after addition of 1.12 kg of 67.5% strength nitric acid (molar fraction 0.47), filtration at room temperature, washing with 67.5% strength nitric acid and drying. Thus 199.6 g of 1-nitroanthraquinone are obtained (yield 71% of theory, purity 90%)

EXAMPLE 7

208 g anthraquinone are nitrated with 2.57 kg of 98% strength nitric acid (molar ratio 40:1) at 20°C during 8 minutes. The reaction is stopped by rapidly distilling off 2.12 kg of nitric acid of 98% strength (molar fraction 0.63). After addition of 0.69 kg of 73% strength nitric acid (molar fraction 0.5) 195.3 g 1-nitroanthraquinone are obtained by filtration at room temperature, washing with 70% strength nitric acid and drying (yield 71% of theory, purity 92%).

We claim:

1. In the process of preparing 1-nitroanthraquinone by nitration of anthraquinone in the presence of nitric acid of at least 90% strength wherein the nitration is carried out at temperatures of 20° to 80°C and the reaction is terminated by lowering the nitric acid molar fraction in the reaction mixture, the improvement consisting of terminating the reaction by distilling off concentrated nitric acid until the nitric acid molar fraction has a value ≤ 0.85.

2. In the process of preparing 1-nitroanthraquinone by nitration of anthraquinone in the presence of nitric acid of at least 90% strength and followed by termination of the nitration by lowering the nitric acid molar fraction, the improvement which comprises distilling of nitric acid from the nitration mixture until the nitric acid molar fraction has a value of ≤ 0.85 and subsequently precipitating 1-nitroanthraquinone by adjusting the nitric acid molar fraction to values of about 0.7 to about 0.4.

3. Process according to claim 2, characterised in that the nitric acid molar fraction is adjusted to values of about 0.7 to about 0.4, to precipitate 1-nitroanthraquinone, by distilling off nitric acid.

4. Process according to claim 2, characterised in that the nitric acid molar fraction is adjusted to values of about 0.7 to about 0.4, to precipitate 1-nitroanthaquinone, by adding water.

5. Process according to claim 2, characterised in that the nitric acid molar fraction is adjusted to values of about 0.7 about 0.4 to precipitate 1-nitroanthraquinone, by adding dilute nitric acid.

* * * * *